United States Patent
Michelson

(10) Patent No.: US 7,314,468 B2
(45) Date of Patent: Jan. 1, 2008

(54) METHOD FOR USING ARCUATE DYNAMIC LORDOTIC GUARD WITH MOVABLE EXTENSIONS FOR CREATING AN IMPLANTATION SPACE POSTERIORLY IN THE LUMBAR SPINE

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 238 days.

(21) Appl. No.: 10/809,149

(22) Filed: Mar. 25, 2004

(65) Prior Publication Data

US 2004/0181233 A1 Sep. 16, 2004

Related U.S. Application Data

(62) Division of application No. 10/085,406, filed on Mar. 1, 2002, now Pat. No. 6,896,680.

(60) Provisional application No. 60/272,382, filed on Mar. 1, 2001.

(51) Int. Cl.
*A61B 17/60* (2006.01)
(52) U.S. Cl. ...................................................... 606/90
(58) Field of Classification Search ................. 606/79, 606/80, 84–86; 623/17.11–17.16
See application file for complete search history.

(56) References Cited

U.S. PATENT DOCUMENTS

| 514,799 A | 2/1894 | Wildt |
| 605,652 A | 6/1898 | Pitt |
| 611,038 A | 9/1898 | Lohman |
| 617,247 A | 1/1899 | Gholson |
| 1,635,137 A | 7/1927 | Mullens |
| 3,486,505 A | 12/1969 | Morrison |
| 4,130,938 A | 12/1978 | Uhlmann |
| 4,545,374 A | 10/1985 | Jacobson |
| 4,690,132 A | 9/1987 | Bayer et al. |
| 5,015,255 A | 5/1991 | Kuslich |
| 5,431,658 A | 7/1995 | Moskovich |
| 5,571,109 A | 11/1996 | Bertagnoli |
| 5,785,647 A | 7/1998 | Tompkins et al. |
| 5,785,648 A | 7/1998 | Min |
| 5,860,973 A * | 1/1999 | Michelson ............... 606/61 |
| 5,876,457 A * | 3/1999 | Picha et al. ............ 623/17.11 |
| 5,885,210 A | 3/1999 | Cox |
| 5,895,426 A * | 4/1999 | Scarborough et al. ... 623/17.16 |
| 5,910,174 A | 6/1999 | Finn |
| 5,951,564 A | 9/1999 | Schroder et al. |
| 6,010,509 A | 1/2000 | Delgado et al. |
| 6,012,363 A | 1/2000 | Minkin |
| 6,063,088 A * | 5/2000 | Winslow ............... 606/61 |
| 6,096,046 A | 8/2000 | Weiss |
| 6,139,563 A | 10/2000 | Cosgrove et al. |
| 6,159,215 A | 12/2000 | Urbahns et al. |
| 6,190,414 B1 * | 2/2001 | Young et al. ............ 623/17.15 |
| 6,210,412 B1 * | 4/2001 | Michelson ............... 606/61 |
| 6,224,604 B1 | 5/2001 | Suddaby |
| 6,309,349 B1 | 10/2001 | Bertolero et al. |

(Continued)

*Primary Examiner*—Eduardo C. Robert
*Assistant Examiner*—James L Swiger
(74) *Attorney, Agent, or Firm*—Martin & Ferraro, LLP

(57) ABSTRACT

A lordotic guard and method for guiding a bone removal device to form an implantation space in the human spine and, if desired, for inserting a spinal implant into the implantation space.

44 Claims, 12 Drawing Sheets

U.S. PATENT DOCUMENTS

| | | |
|---|---|---|
| 6,494,883 B1 | 12/2002 | Ferree |
| 6,520,967 B1 | 2/2003 | Cauthen |
| 2002/0111680 A1 | 8/2002 | Michelson |
| 2002/0123753 A1 | 9/2002 | Michelson |
| 2003/0023209 A1* | 1/2003 | Gruskin et al. ............ 604/290 |
| 2003/0135220 A1* | 7/2003 | Cauthen ...................... 606/87 |
| 2003/0199874 A1 | 10/2003 | Michelson |
| 2003/0229401 A1* | 12/2003 | Mansouri et al. ........ 623/23.71 |
| 2004/0073309 A1 | 4/2004 | Bianchi et al. |
| 2004/0082958 A1 | 4/2004 | Michelson |

\* cited by examiner

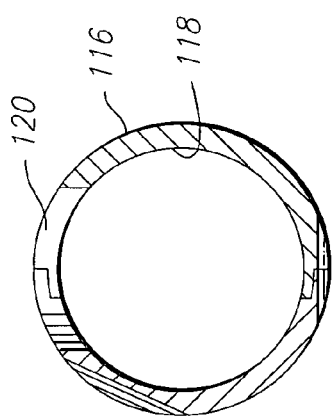
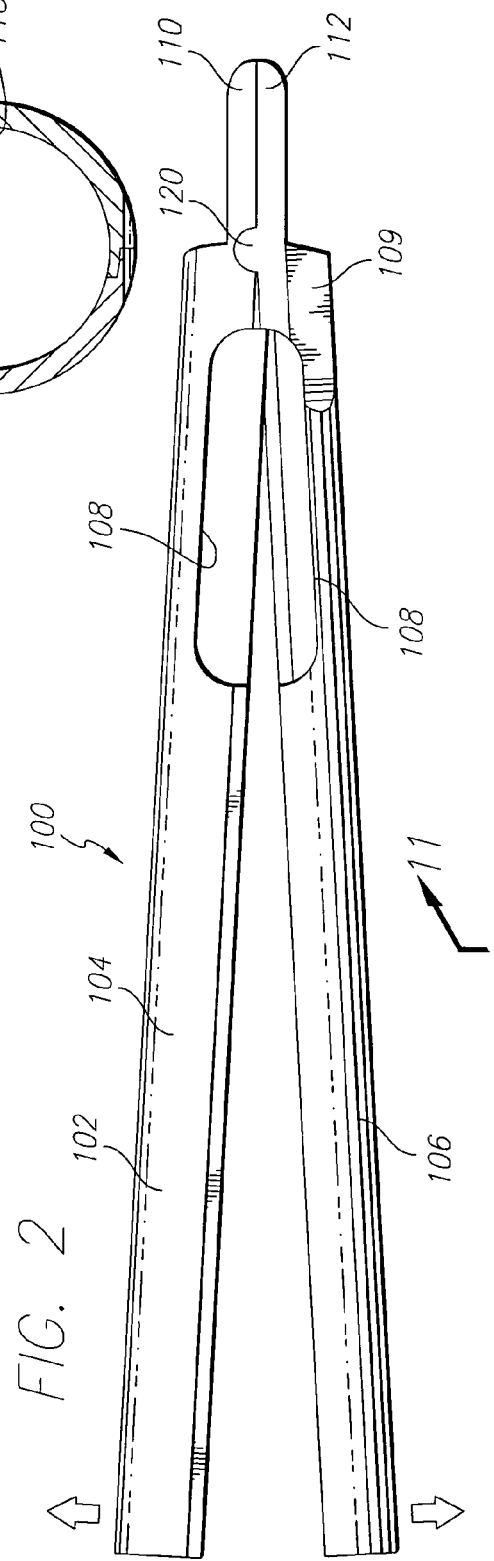
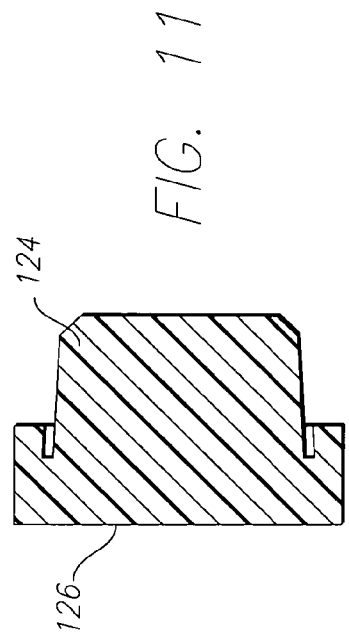
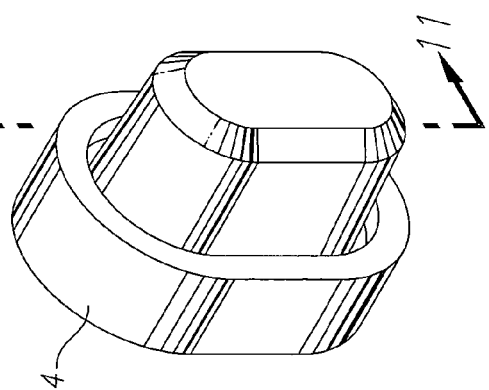

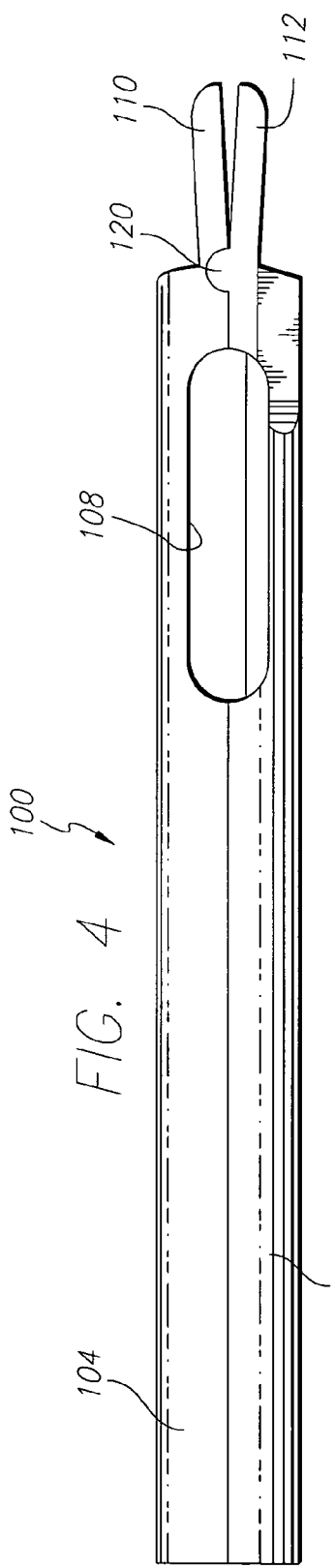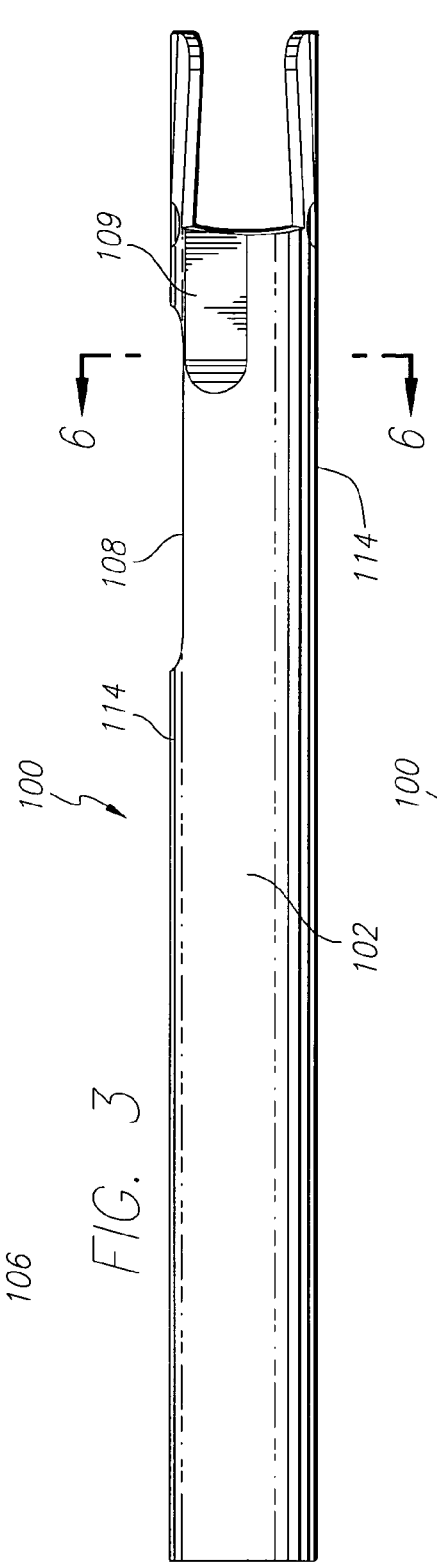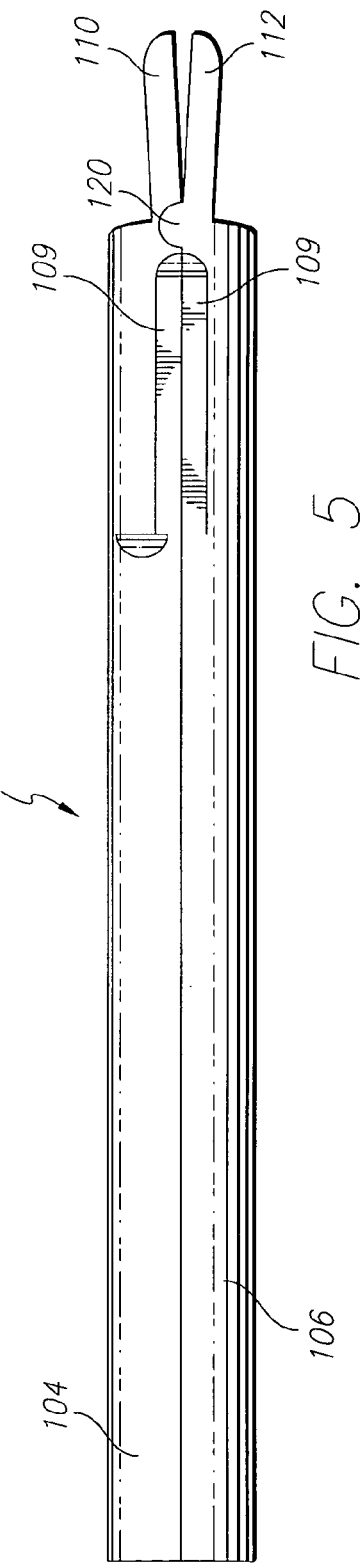

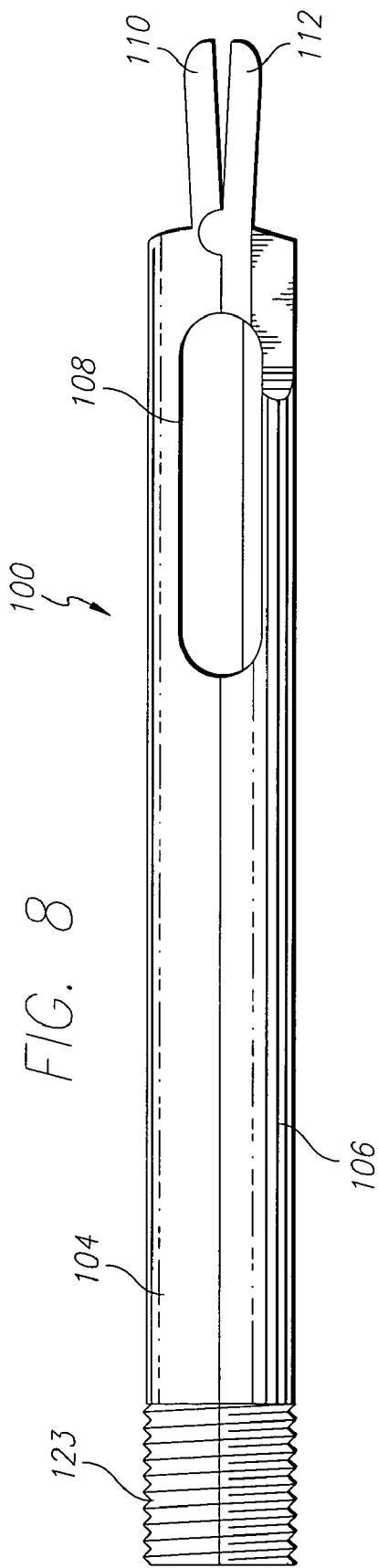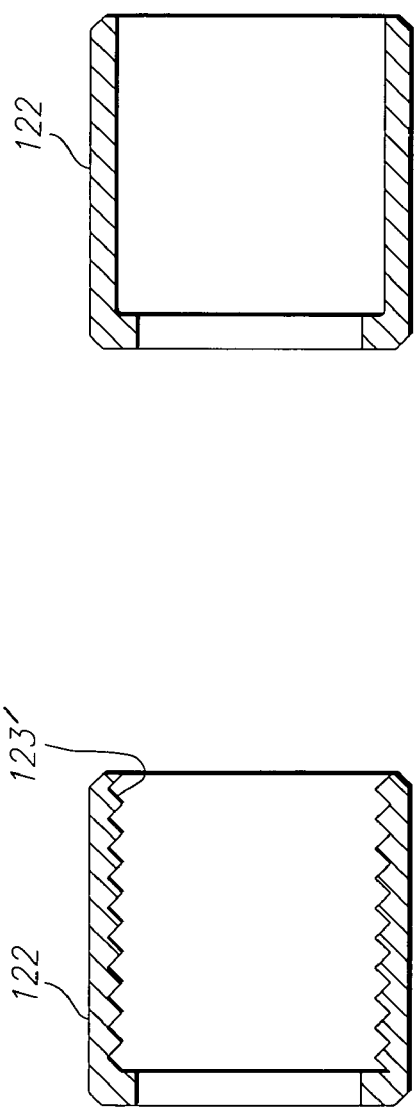

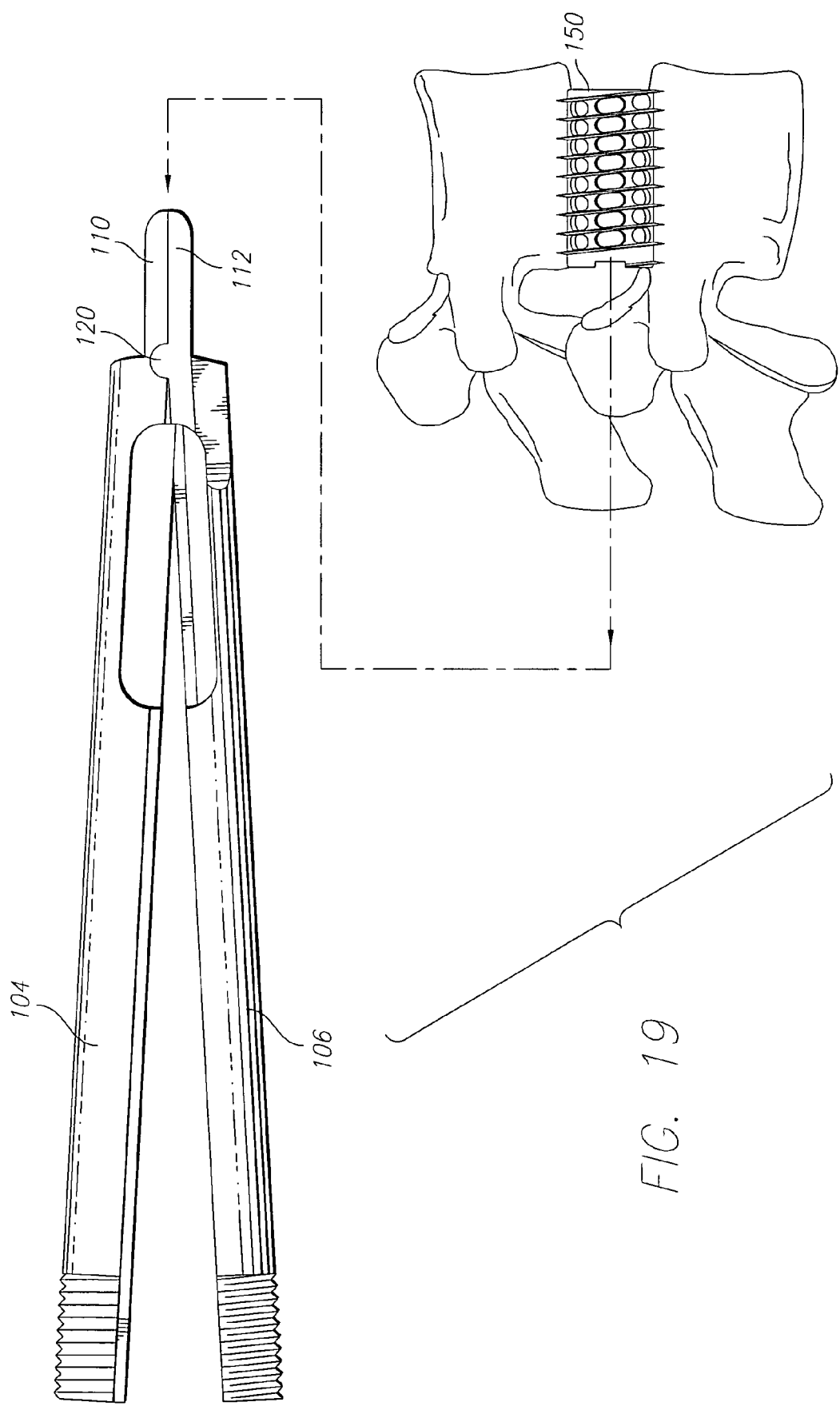

METHOD FOR USING ARCUATE DYNAMIC LORDOTIC GUARD WITH MOVABLE EXTENSIONS FOR CREATING AN IMPLANTATION SPACE POSTERIORLY IN THE LUMBAR SPINE

This application is a divisional of application Ser. No. 10/085,406, filed Mar. 1, 2002, now U.S. Pat. No. 6,896,680 which claims the benefit of U.S. provisional Application No. 60/272,382, filed Mar. 1, 2001; all of which is incorporated herein by reference.

FIELD OF THE INVENTION

The present invention relates to a device for implantation into a disc space between adjacent vertebral bodies in the human spine, and a device and method for working on those portions of the vertebral bodies adjacent that disc space to remove bone material and thereby access vascular bone, and preferably a device and method for protecting the neurological structures such as nerve roots and dural sac proximate the implantation site while providing protected access to form an implantation space and then access the implantation space formed between the adjacent vertebral bodies for insertion therein of an implant having upper and lower surfaces being at least in part arcuate. The device and associated method are used to position (space apart and align) the vertebral bodies, guide the formation of a surface into or through each of the vertebral body surfaces that are adjacent the intervertebral disc space, and may further be utilized to guide an interbody spinal implant having upper and lower surfaces being at least in part arcuate into the implantation space.

In one embodiment, the device and associated method are used to make an implantation space to insert an implant of a height having a known correspondence to the height of the space created. In another embodiment, the device and associated method are used to make an implantation space of known and specific dimensions (e.g., width; depth; and height) and with certain preferred embodiments, permit passage through the device of an implant having a height greater than the height of the implantation space formed through the device.

BACKGROUND OF THE INVENTION

Human vertebral bodies are comprised of a dense, hard outer shell and a relatively less dense inner mass. The hard outer shell is very densely compacted cancellous bone, resembling cortical bone at all but high magnification, and is generally referred to as the cortex. The inner mass is a softer cancellous bone. As shown in FIG. 1, the outer shell of cortex bone (the bony endplate) that is adjacent the disc and the bone immediately beneath that bone (both are subchondral, that is, beneath the cartilage layer or cartilaginous endplate that separates the bone from the disc), are defined for the specific purposes of this specification to comprise the "end plate region" to avoid any confusion that might otherwise arise from any inconsistency in the use of any of these terms. While it is understood that these terms may have other meanings more ordinary or special, and that those of ordinary skill in the art might otherwise differ as to the correct meanings of these terms, it is exactly for the purpose of removing any ambiguity that these terms are being so precisely defined specifically for this specification.

The spinal disc that resides between adjacent vertebral bodies maintains the spacing between those vertebral bodies and, in a healthy spine, allows for relative motion between the vertebrae. At the time of surgery, for example in the instance of interbody fusion, that is, where fusion is intended to occur between adjacent vertebral bodies of a patient's spine, the surgeon typically prepares an opening at the site of the intended fusion by removing a substantial amount of the nucleus disc material that exists between the adjacent vertebral bodies to be fused. Because the outermost layers of bone of the vertebral end plate are relatively inert to new bone growth, the surgeon will typically work on the end plate to remove at least the outermost cell layers of bone to gain access to the blood-rich, vascular bone tissue within the vertebral body. In this manner, the vertebrae are prepared in a way that encourages new bone growth consistent with fusion.

Devices for assisting a surgeon in accessing the disc space and adjacent vertebral bodies are known. Drill guides and boxed chisels have been used to form an implantation space between the adjacent vertebral bodies for insertion of a spinal implant therein. Applicant invented a guard and instrument system particularly well suited for use in the lumbar spine and of unequalled advantage for use posteriorly therein through which both the implantation space can be formed and a spinal implant can be inserted into the implantation space, as disclosed in U.S. Pat. No. 5,015,247, filed Jun. 13, 1988, which is hereby incorporated by reference.

Applicant also invented a guard having disc penetrating extension(s), which extensions have utility for stabilizing the guard, stabilizing the adjacent vertebrae relative to each other, urging the vertebrae apart if desired, and aligning the vertebrae to each other if desired to form the implantation space through the guard and insert the spinal implant through the guard into the implantation space, as disclosed in U.S. Pat. No. 6,080,155 filed Feb. 27, 1995, incorporated herein by reference. The disc penetrating extensions can have either parallel or angled upper and lower surfaces in contact with the adjacent vertebral bodies to place the adjacent vertebral bodies parallel to one another or at an angle to one another. The disclosed disc penetrating extensions are rigid.

To obtain a particular orientation between the adjacent vertebral bodies a surgeon selects a guard having a predetermined orientation between the upper and lower surfaces of the disc penetrating extensions. In the case of disc penetrating extensions that have upper and lower surfaces diverging from one another as would be useful for posterior lumbar interbody fusion (PLIF), so as to be higher at the insertion or distal end than at the trailing or proximal end of the extensions, a tapered leading end is used to facilitate insertion of the disc penetrating extensions into the disc space. Such a configuration allows for lordosis of the lumbar segment of a spine to be operated upon from a posterior approach. For extensions that have diverging upper and lower surfaces, additional force is required to drive the guard and extensions into place. Then, after an implant is inserted, it may be difficult to remove a distractor element such as a guard having disc penetrating extensions having a maximum height greater then the height of the disc space posterior height.

Present methods of forming the implantation space between adjacent vertebral bodies generally include the use of one or more of the following: hand held biting and grasping instruments known as rongeurs; drills and drill guides; rotating burrs driven by a motor; and osteotomes and chisels. Applicant has taught various novel instruments to mill out the recipient fusion site across the height of the disc space including various cutting/milling frames and various novel cutters as disclosed in applicant's U.S. application Ser. No. 08/688,758, incorporated herein by reference.

The surgeon must work upon the adjacent end plates of the adjacent vertebrae to access the vascular, cancellous bone that is best suited for participating in the fusion and causing active bone growth, and also to attempt to obtain an appropriately shaped surface in the vertebral bodies to receive the implant. Because the end plates of the adjacent vertebrae are not flat, but rather have a complex biological as opposed to geometrical curved shape, it is necessary to conform the vertebrae to the shape of the implant to be received therebetween.

There is a need for a guard for use in posterior lumbar surgery to create an interbody implantation space while providing for spinal lordosis and while being easily and safely inserted and as easily and safely removed.

SUMMARY OF THE INVENTION

In accordance with the purposes of the present invention, as embodied and broadly described herein, a guard of this invention is provided for use in spinal surgery across a disc space between two adjacent vertebral bodies of a human spine. The guard includes a body having a leading end and an opposite trailing end. The body has a first portion and a second portion proximate the leading end that are in pivotal relationship to one another between an open position and a closed position. The first and second portions each have opposed interior portions that are at least in part arcuate and define an opening for providing protected access to the disc space and the adjacent vertebral bodies. The opposed interior portions are adapted to guide a bone removal device therethrough that is sized to form an implantation space across the disc space and at least in part into the adjacent vertebral bodies. The guard also includes at least one disc space penetrating extension extending from the leading end of the body that is adapted for insertion at least in part into the disc space. The extension has a first portion extending from the first portion of the body that has a contact surface adapted to bear against one of the adjacent endplates of the adjacent vertebral bodies. The extension also has a second portion extending from the second portion of the body that has a contact surface adapted to bear against the other of the adjacent endplates of the adjacent vertebral bodies. The contact surfaces of the first and second portions of the extension are in pivotal relationship to one another from an insertion position to a deployed position to move the adjacent vertebral bodies apart upon movement of the first and second portions of the body from the open position to the closed position.

The body of the guard may have a generally rectangular or generally square cross section along at least a portion of the length of the body. The leading end of the body may be adapted to conform at least in part to the exterior surfaces of the adjacent vertebral bodies by having the leading end cut back to permit the contact surfaces to have an intimate fit with the vertebral bodies when the guard is in the deployed position. The body may include at least one window adapted to permit the surgeon to observe the surgery though the window and/or permit portions of bone extending though the window to be removed by the bone removal device passing through the body of the guard.

The guard may include a second disc penetrating extension diametrically opposite to a first disc penetrating extension. Each disc penetrating extension may have a tapered leading end and have contact surfaces that are parallel to each other over a substantial portion of the length of each extension when in the insertion position. The first and second portions of each disc penetrating extension may be adapted to touch one another when in the insertion position.

The first and second portions of the body may be hinged to one another to rotatably articulate relative to one another about an axis of rotation that is fixed relative to the mid-longitudinal axis of the guard when moved from the open position to the closed position. The body may have an interior surface having a cooperating surface for guiding a corresponding cooperating surface on the bone removal device.

The guard may include an impaction cap adapted to cooperatively engage the trailing end of the body when the body is in the open position. The guard may include a lock in the form of a collar adapted to cooperatively engage the body of the guard when the body is in the closed position to hold the body in the closed position.

The guard may form part of a combined spinal surgery set that includes a bone removal device, an implant driver, and a spinal implant, or any combination thereof. The bone removal device may be a drill, mill, or any other device suitable for the intended purpose. The implant may be sized and shaped to at least in part match the space formed in the spine by the bone removal device and may be adapted to be combined or treated with a natural or artificial bone growth promoting material or substance.

In accordance with the purposes of another embodiment of the present invention, as embodied and broadly described herein, a guard of this invention is provided for use in spinal surgery across a disc space between two adjacent vertebral bodies of the human spine. The guard includes a body having an opening for providing protected access to the disc space and the adjacent vertebral bodies. The opening has opposed interior portions that are at least in part arcuate and adapted to guide therethrough a bone removal device sized to form an implantation space across the disc space and at least in part into the adjacent vertebral bodies. The guard also includes at least one disc space penetrating extension extending from the body that is adapted for insertion at least in part into the disc space. The disc penetrating extension has a first portion having a contact surface adapted to bear against one of the adjacent endplates of the adjacent vertebral bodies and a second portion having a contact surface adapted to bear against the other of the adjacent endplates of the adjacent vertebral bodies. The contact surfaces of the first and second portions are adapted to rotatably articulate relative to one another between an insertion position and a deployed position to move the adjacent vertebral bodies apart.

The body has a leading end and an opposite trailing end. The body may have a first portion and a second portion proximate the leading end that are adapted to rotatably articulate relative to one another between an open position and a closed position.

In accordance with the purposes of a further embodiment of the present invention, as embodied and broadly described herein, a method of this invention is provided for inserting a spinal implant having at least in part arcuate upper and lower portions at least in part within and across the generally restored height of a disc space between two adjacent vertebral bodies of a human spine. The method includes the steps of positioning into the disc space between the adjacent vertebral bodies a guard having a body and an extension for insertion at least in part into the disc space and for bearing against end plates of the adjacent vertebral bodies to restore the spacing of the disc space between the adjacent vertebrae, the guard having a first portion oriented toward one of the adjacent vertebral bodies and a second portion oriented toward another of the adjacent vertebral bodies, the first and second portions being rotatably articulating relative to one another such that when the body moves from an open position to a closed position the extension moves from an insertion position to a deployed position to move the adjacent vertebral bodies apart; rotatably articulating the guard to move the body from the open position to the closed position and the extension from the insertion position to the deployed position to move the adjacent vertebral bodies apart; and forming, through the guard, an opening across height of the disc space and into at least a portion of the endplates of the adjacent vertebral bodies, the opening formed into the endplates having at least in part arcuate surfaces.

The method may include the further steps of performing the spinal implant surgery from a position posterior to the transverse processes of the vertebrae adjacent the disc space; performing the procedure on both sides of the spinal midline of the spine; securing the body of the guard in the closed position; and inserting two implants into the spine.

The positioning step may include the further steps of positioning a guard having multiple extensions for insertion into the disc space; placing the body of the guard in the open position; driving the extension into the disc space; and inducing angulation to the adjacent vertebral bodies relative to one another.

The rotatably articulating step may include the further steps of orienting the adjacent vertebral bodies in a predetermined relationship relative to each other; and inducing lordosis to the adjacent vertebral bodies.

The forming step may include the further steps of inserting the bone removal device through the guard to a desired depth; forming the implantation space with the bone removal device; and forming opposed receiving surfaces in the end plates of the vertebral bodies corresponding at least in part in size, shape, and contour to an implant to be implanted. The forming step may include any one of milling, drilling, reaming, and trephining the implantation space.

The method may include the further steps of inserting the implant into the implantation space through the guard, or inserting the implant into the implantation space after removing the guard from the disc space. The inserting step may include the further steps of inserting the implant using an implant inserter; and removing the implant inserter after using the implant inserter to insert the implant into the implantation space. The inserting step may also include inserting a spinal implant that is a spinal fusion implant that has at least in part arcuate upper and lower surfaces for placement between and in contact with the adjacent vertebral bodies, each of the upper and lower surfaces having at least one opening adapted to permit for the growth of bone from adjacent vertebral body to adjacent vertebral body through the implant. The inserting step may include inserting a spinal implant having a hollow between the upper and lower surfaces; inserting a spinal implant that is expandable; and inserting a spinal implant having surface projections configured to resist expulsion of the implant from the implantation space. The inserting step may include inserting any one of an inert spacer, an artificial disc, or a bone graft.

The inserting step may further include the steps of compressively loading the implant with fusion promoting substances selected from one of bone, bone derived products, demineralized bone matrix, ossifying proteins, bone morphogenetic protein, hydroxyapatite, and genes coding for the production of bone; and retaining the fusion promoting substance within the implant after the loading step. The step of retaining the fusion promoting substance may include attaching a cap to the implant.

The inserting step may also include the steps of treating the implant with a fusion promoting substance; inserting an implant in combination with a chemical substance adapted to inhibit scar formation; inserting an implant in combination with an antimicrobial material; inserting an implant including a fusion promoting substance or having a bone ingrowth surface; inserting an implant being at least in part of one of bone and bone growth promoting material; and inserting an implant in combination with at least one of a fusion promoting substance, bone, bone growth promoting material, bone derived products, demineralized bone matrix, ossifying proteins, bone morphogenetic protein, hydroxyapatite, and genes coding for the production of bone.

The method may further include the steps of collapsing the extensions and removing the guard form the disc space.

The accompanying drawings, which are incorporated in and constitute a part of this specification, are by way of example only and not limitation, and illustrate several embodiments of the invention, which together with the description, serve to explain the principles of the invention. The scope of the invention is limited only by the scope of the claims as from the present teachings other embodiments of the present invention shall be apparent to those skilled in the art.

OBJECTS OF THE PRESENT INVENTION

The present invention has a number of embodiments, at least some of which have as an object of at least one embodiment of the present invention to provide a device and method for quickly, safely, effectively, and accurately spacing apart and positioning a pair of adjacent vertebral bodies to receive an implant, which is anything designed to be left in the body for an extended length of time, working upon the properly positioned vertebral body end plate regions adjacent a disc space so as to, remove bone to produce a receiving surface having an arcuate configuration corresponding to an implant having upper and lower surfaces being at least in part arcuate to be implanted between the adjacent vertebrae.

It is a further object of at least one embodiment of the present invention to provide a device and method that permits the insertion of disc penetrating extensions of a guard into the disc space posteriorly in a first position that facilitates insertion and removal of the disc penetrating extensions into and from the disc space and then permits the disc penetrating extensions to be moved into a second position that orients the adjacent vertebral bodies in a preferred lordotic relationship relative to the device and each other.

It is a further object of the present invention, in at least certain embodiments, to provide a device capable of working upon both of the vertebral body end plate regions adjacent a disc space to produce opposed arcuate receiving surfaces in the adjacent end plates corresponding at least in part in size, shape, and contour to an implant to be implanted with the exception of the height of the implant, which may be greater than the distance between the opposed receiving surfaces that may be distracted or otherwise moved apart by insertion of the implant, and in so doing to define the shape to the implantation space.

It is a further object of the present invention to provide a device that works with linear insertion, i.e., insertion along a single axis, and without removing the device during the process of disc space preparation and, if so desired with certain embodiments of the present invention, implant placement.

These and other objectives of the present invention will occur to those of ordinary skill in the art based on the description of the preferred embodiments of the present invention described below. However, not all embodiments of the inventive features of the present invention need achieve all the objectives identified above, and the invention in its broadest aspects is not limited to the preferred embodiments described herein.

BRIEF DESCRIPTION OF THE DRAWINGS

The accompanying drawings together with the description, serve to explain the objects, advantages, and principles of the invention. In the drawings:

FIG. 2 is a side view of a preferred embodiment of a guard of the present invention with the disc penetrating extensions closed into a first or insertion position;

FIG. 3 is a bottom view of the guard shown in FIG. 2;

FIG. 4 is a side view of the guard of FIG. 2 with the disc penetrating extensions opened into a second or deployed position;

FIG. 5 is an opposite side view of the guard of FIG. 2 with the disc penetrating extensions opened into a second or deployed position;

FIG. 6 is a cross-sectional view of the guard shown in FIG. 3 taken along line 6-6 of FIG. 3;

FIG. 7 is side cross-sectional view of a lock collar for use with the guard of FIGS. 4 and 5;

FIG. 8 is a side view of an alternative embodiment of a guard with the disc penetrating extensions opened into a second or deployed portion;

FIG. 9 is a side cross-sectional view of a lock collar for use with the guard of FIG. 8;

FIG. 10 is a perspective view of an impaction cap for use with the guard of FIG. 2 or FIG. 8;

FIG. 11 is a cross-sectional view of the impaction cap of FIG. 10 taken along line 11-11 of FIG. 10;

FIG. 19 shows a side view of the spinal segment with the implant of FIG. 15 inserted in the disc space and the guard with the disc penetrating extensions in a first position to facilitate the removal of the guard.

DETAILED DESCRIPTION OF THE PRESENTLY PREFFERED EMBODIMENT

Figure 1:
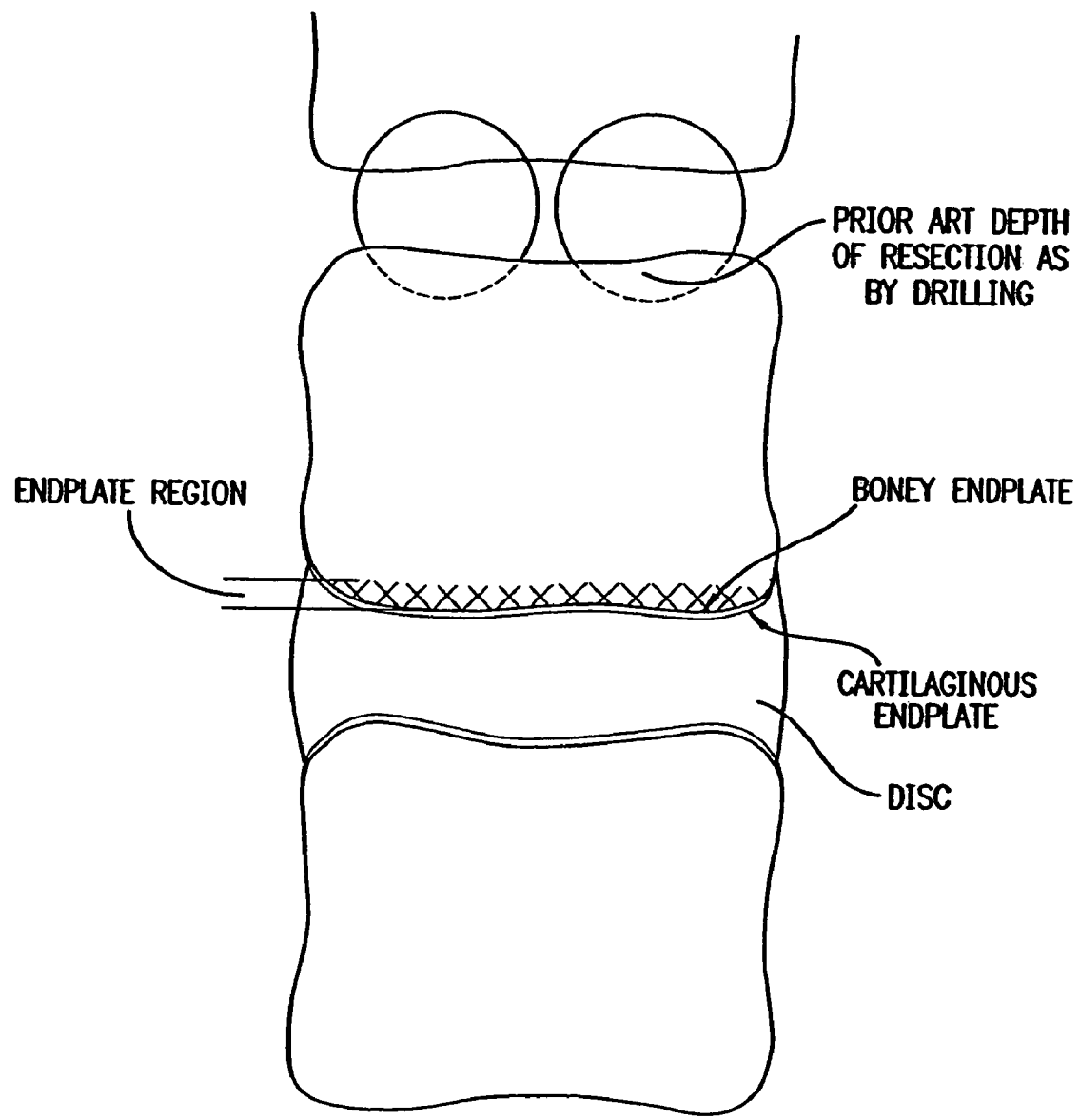
FIG. 1 is a top plan view of a horizontal cross section through a bony end plate region of a vertebral body.

Reference will now be made in detail to the present preferred embodiments of the invention, as illustrated in the accompanying drawings.

FIGS. 2-5 are generally directed to an embodiment of a guard having a circular cross-section or having opposed upper and lower arcuate portions for use in spinal surgery for forming an implantation space between adjacent vertebral bodies of the lumbar spine from a posterior approach. As shown in FIG. 2, a guard 100 has a body 102 with a first portion 104 and a second portion 106. Guard 100 also has disc penetrating extensions 110, 112. In particular, first disc penetrating extension 110 extends from first portion 104 of body 102 and second disc penetrating extension 112 extends from second portion 106 of body 102.

In preferred embodiments, but not requisite, various windows 108 in guard body 102 allow the surgeon to remove portions of a facet, pedicle, or spinous process in the same procedure as the bone removal of the vertebral bodies for creating an insertion space therebetween. It is within the scope of the present invention to use a variety of window shapes in addition to the shape depicted to accommodate projecting bone structures. Window 108 also may be used in observing the procedure at various stages of the operation and if so desired for passing instruments therethrough. Rather than or in addition to a window 108, as best shown in FIGS. 2-5 and 8, the guard may have one or more indentations 109 of the wall of the body 102 to make room for a facet, pedicle, or spinous process. Indentation 109, shown in FIG. 3, allows guard 100 to clear the pedicle of the lower vertebra. Indentation 109, shown in FIG. 5, avoids interference with the bulge of the spinous process. Alternatively, indentation 109 of FIG. 5 could be a window to allow bone to protrude inside of guard 100 to be cut off during the drilling step of the surgical procedure. As best seen in top view FIG. 3, disc-penetrating extensions 110, 112 are preferably at least in part coextensive with the sides 114 of body 102.

FIG. 2 shows guard 100 with body 102 with disc penetrating extensions 110, 112 in a first or closed position, for insertion into the disc space between adjacent lumbar vertebral bodies to be operated upon. Whereas FIGS. 4, 5, and 8 show guard 100 with body 102 closed and disc penetrating extensions 110, 112 in a second or expanded or deployed position. FIG. 6 shows a cross-sectional view of guard 100 with exterior surface 116, interior surface 118, and hinges 120.

FIG. 7 is a side cross-sectional view of a lock collar 122 for use with guard 100 of FIG. 2. Lock collar 122 is used when body 102 of guard 100 is in the closed position to lock guard 100 into that position.

FIG. 8 is a side view of an alternative embodiment of guard 100 including a threaded end 123 for receipt of lock collar 122 of FIG. 9 having matching threads 123'.

A perspective view of an impaction cap 124 for use with guard 100 is shown in FIG. 10. FIG. 11 is a cross-sectional view of impaction cap 124. Impaction cap 124 is fit over the proximal or trailing end of guard 100 with body 102 in the open position and disc penetrating extensions 110, 112 in the closed, first, or insertion position. While it may be possible to insert the extensions of the guard into the disc space by holding the body of guard 100, impaction cap 124 provides a contact surface 126 upon which force can be applied, such as with a mallet, to drive disc penetrating extensions 110, 112 of guard 100 into the disc space between adjacent vertebral bodies.

FIGS. 12-19 show the progression of various steps of a preferred method for using guard 100 and other associated equipment disclosed herein.

Figure 12:
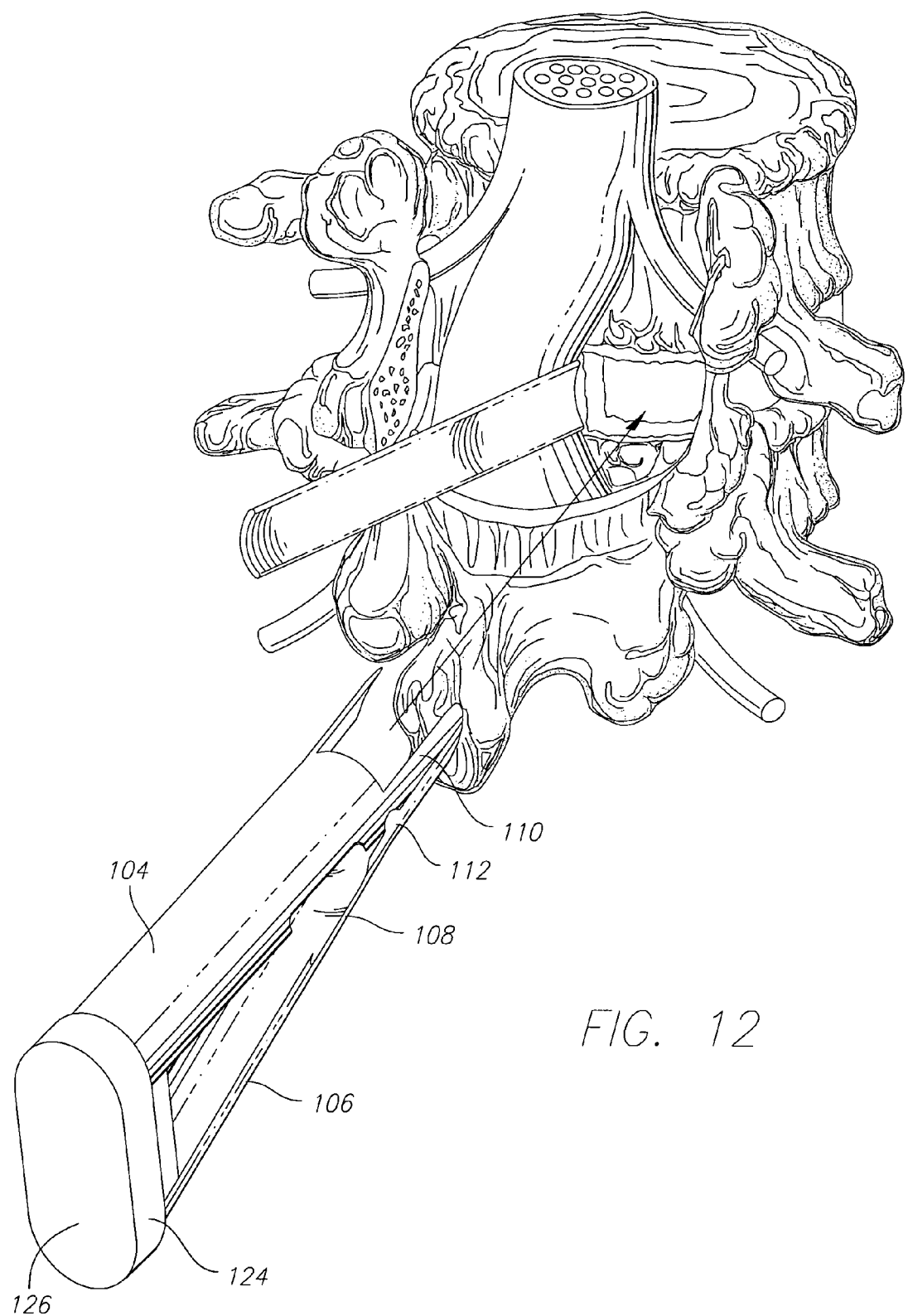
FIG. 12 is a rear perspective view of a lumbar segment of a spine with the dural sac retracted to the left showing a partial discectomy and the guard with disc penetrating extensions of FIG. 2 approaching the disc space between the adjacent vertebral bodies with the disc penetrating extensions in the first or insertion position.

FIG. 12 is a perspective view of a segment of a spine viewed from a posterior aspect with the dural sac retracted to the left showing that a partial discectomy has already been performed. Guard 100 with disc penetrating extensions 110, 112 are shown approaching the disc space between the adjacent vertebral bodies with disc penetrating extensions 110, 112 in the first or insertion position. Impaction cap 124 is positioned on the proximal or trailing end of guard 100 to maintain it in the open position such that the disc penetrating extensions are closed into the insertion position. In this position, guard 100 is ready to be placed or driven into the disc space between the adjacent vertebral bodies.

Figure 13:
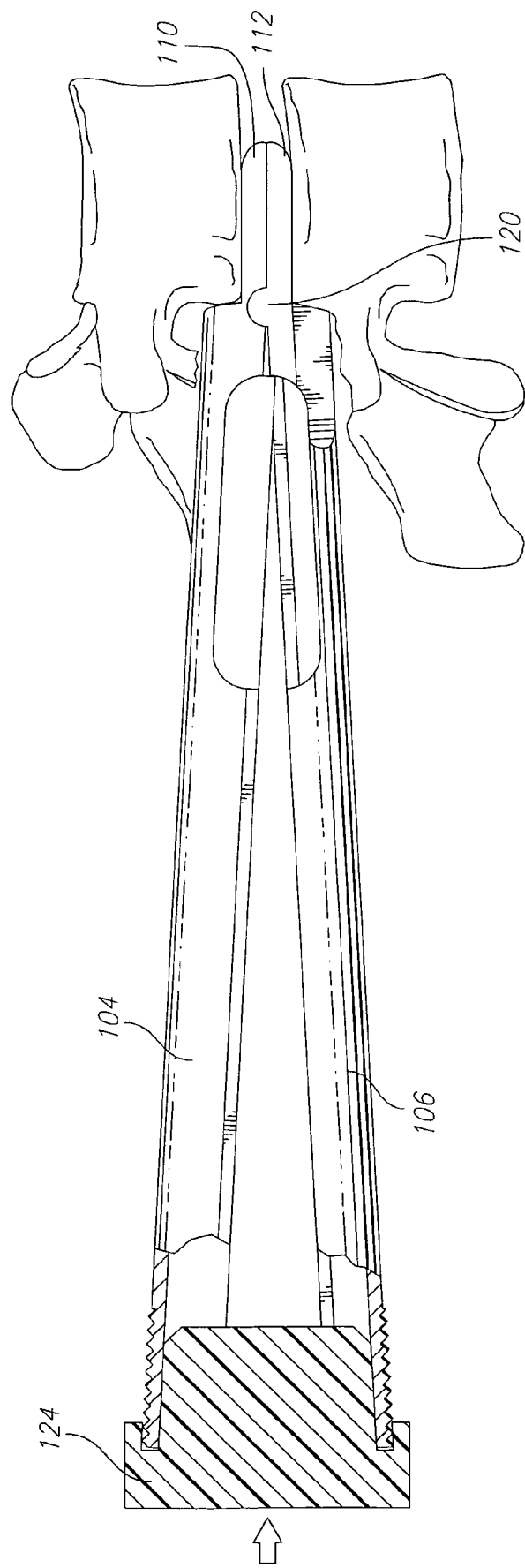
FIG. 13 is a side view of the guard of FIG. 8 inserted fully within the spine with the disc penetrating extensions parallel to one another in the first or insertion position with the impaction cap of FIG. 10 and a portion of the guard in cross-section on the distal end of the guard.

In FIG. 13, the extensions of guard 100 are fully inserted into the spine with the disc penetrating extensions parallel to one another in the first or insertion position. Impaction cap 124 is shown holding the guard in the open position and the disc penetrating extension in the first or insertion position. While the disc penetrating extensions of the first position are shown with a parallel orientation to one another, it is anticipated that the disc penetrating extensions may also be at an angle to one another in the first or closed position. Guard 100 rotationally articulates to permit movement of disc penetrating extensions 110, 112 in response to movement of first portion 104 and second portion 106 of body 102 relative to one another. The rotational articulation preferably occurs about hinge 120, which is preferably formed in first and second portions 104, 106 of body 102.

Figure 14:
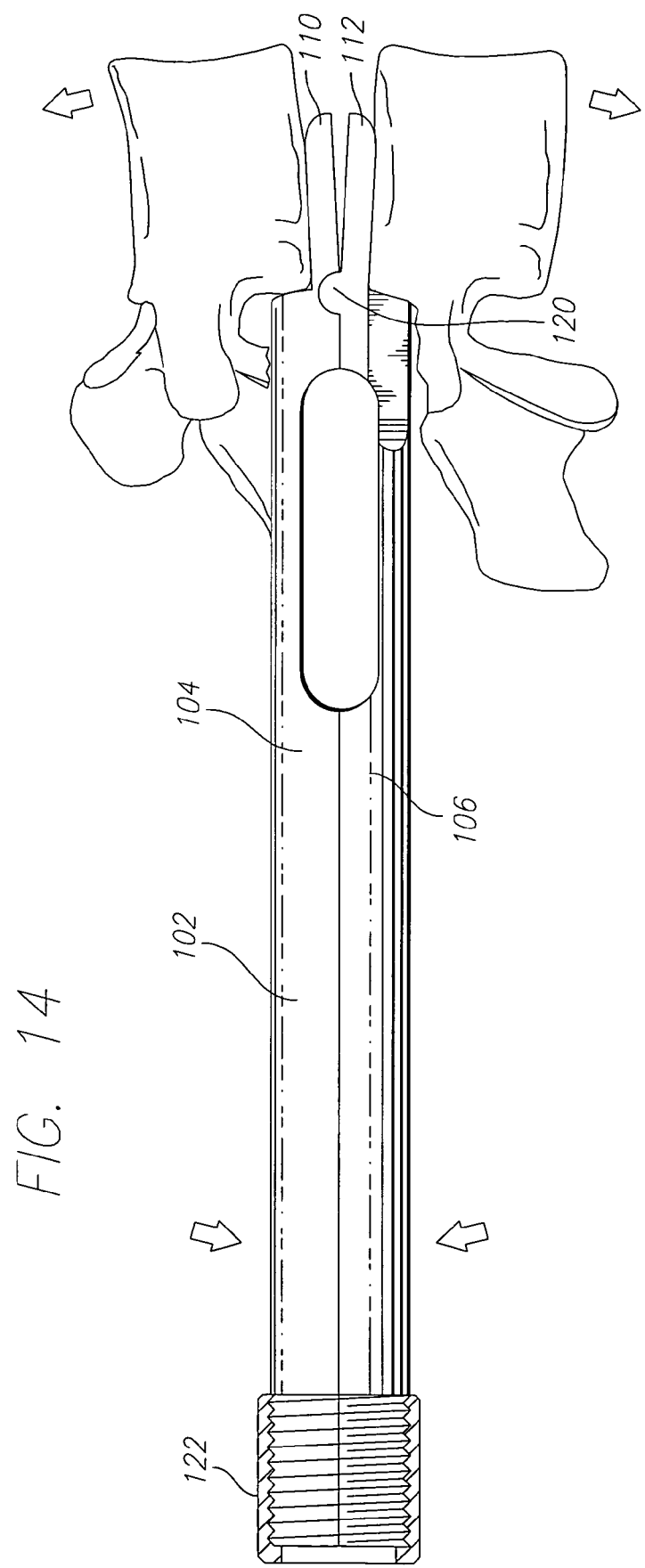
FIG. 14 is a side view of the guard of FIG. 8 in the deployed position with the disc penetrating extensions shown in the second or expanded position to induce lordosis to the vertebral bodies and the proximal or trailing end of the guard shown in partial cross-section with the locking cap of FIG. 9 assembled to maintain the guard in a closed position.

In FIG. 14, body 102 of guard 100 is shown in a closed position with the disc penetrating extensions shown in the second, open or inserted position to induce lordosis to the vertebral bodies. After closing the body of guard 100, the proximal or trailing end has lock collar 122 placed around it to maintain the body of guard 100 in the closed position. The axis of rotation through hinge 120 is at the back of the adjacent vertebral bodies.

Figure 15:
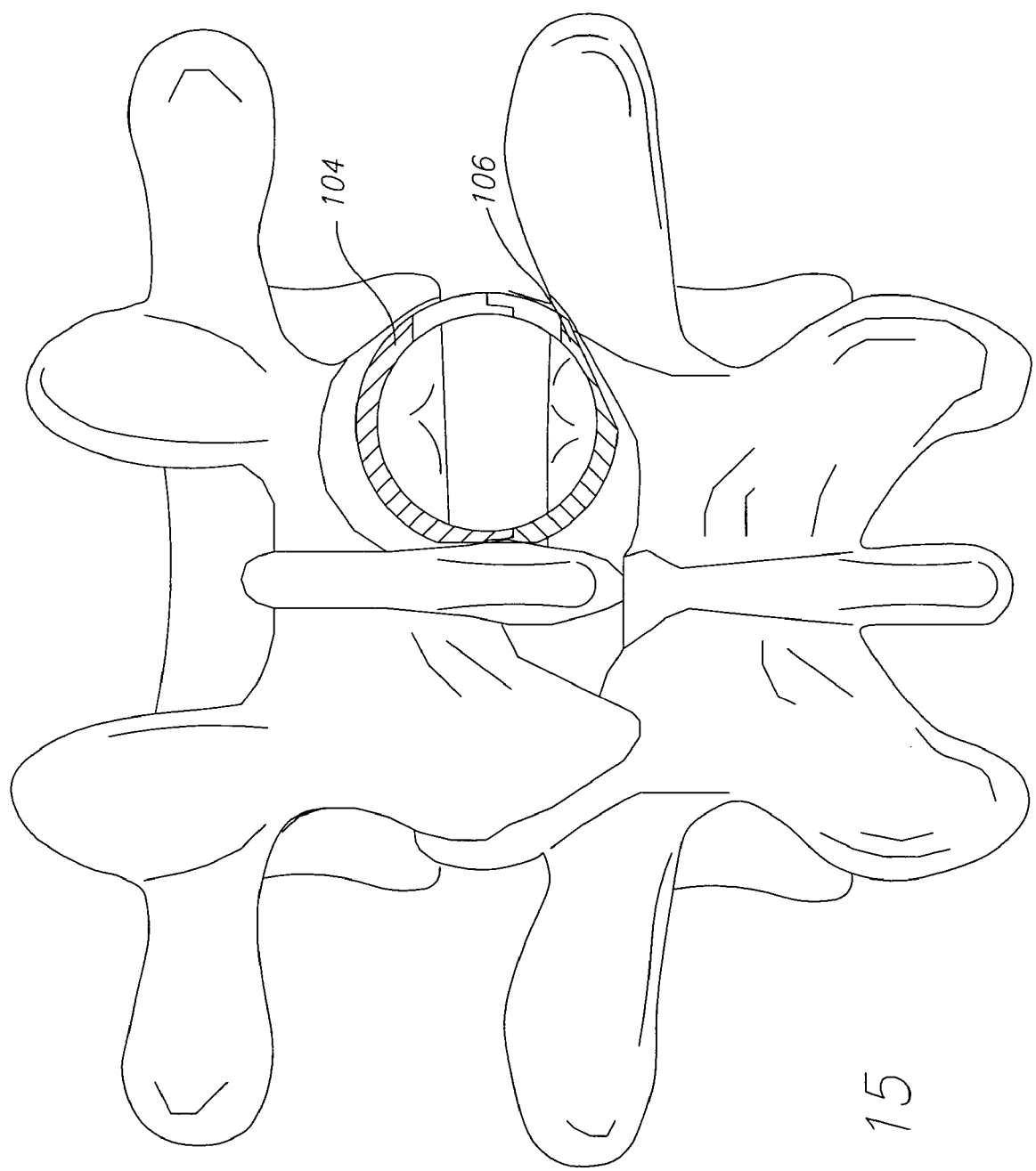
FIG. 15 shows a proximal end view of a guard in the deployed position between adjacent vertebral bodies with portions of the end plates of the adjacent vertebral bodies visible through the interior of the guard of FIG. 8.

FIG. 15 shows a proximal end view of guard 100 with the body in the closed and inserted position between adjacent vertebral bodies with portions of the end plates of the adjacent vertebral bodies visible through the interior of guard 100.

Figure 16:
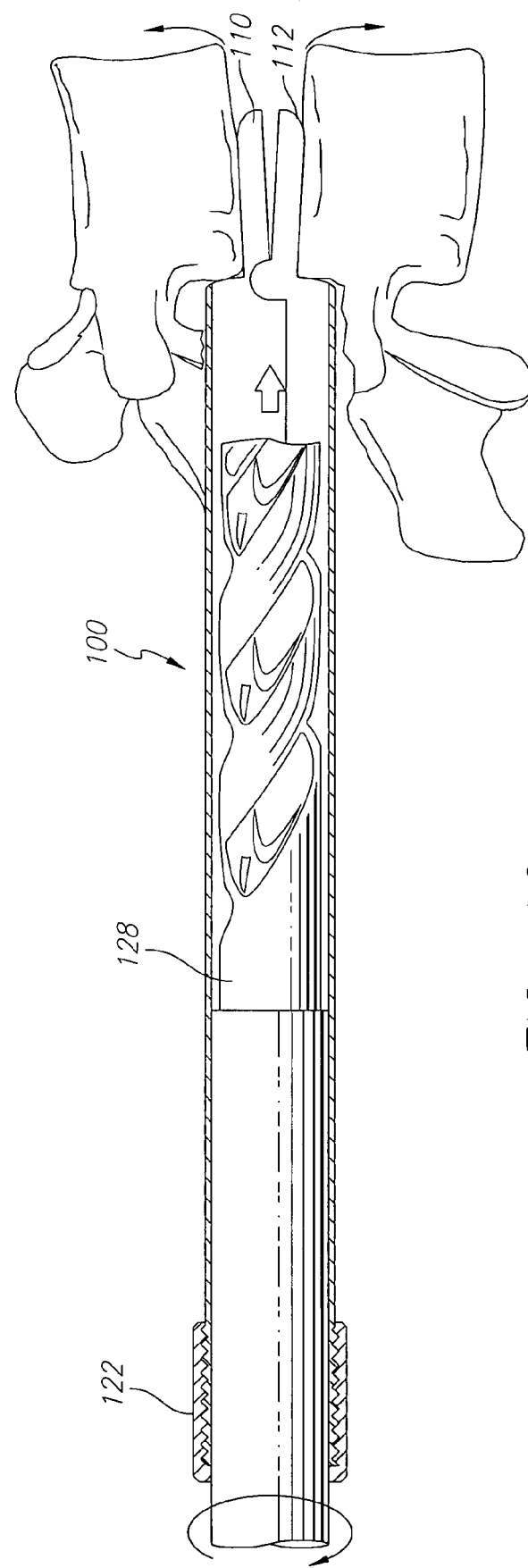
FIG. 16 shows a side view of the guard of FIG. 8 in the deployed position with the disc penetrating extensions in an expanded position to induce angulation to the adjacent vertebral bodies and the distal end of the guard shown in cross-section to show a side view of a drill being inserted through the guard of FIG. 8.

In FIG. 16 the body of guard 100 is in a closed position with disc penetrating extensions 110, 112 in the second, expanded or inserted position to induce angulation to the adjacent vertebral bodies. At the distal end of guard 100 shown in cross-section is a side view of drill 128 being inserted through guard 100. Guard 100 provides protected access to the disc space and the adjacent vertebral bodies for drill 128 via the elongated opening in guard 100. In one embodiment shown in FIGS. 18 and 19, threaded implant 150 having a body sized to match the space formed in the spine by drill 128 is screwed into the adjacent vertebral bodies. Drill 128 may have a reduced diameter cutting portion relative to the shaft diameter or may be inserted through an inner sleeve that passes into guard 100 to guide drill 128 to form an implantation space smaller than the passage through guard 100. Thus, the guard opening may be taller than the height of the cutting portion of drill 128. Such a taller opening also allows the implantation of an implant 150 taller than the height of the cutting portion of drill 128. For example, a taller oval implant or one with truncated sides may be linearly inserted into the implantation space having arcuate cuts into the adjacent vertebral bodies. Implant 150 may be threaded, ratcheted, knurled, or have any other surface projections to facilitate engaging the adjacent vertebral bodies.

Figure 17:
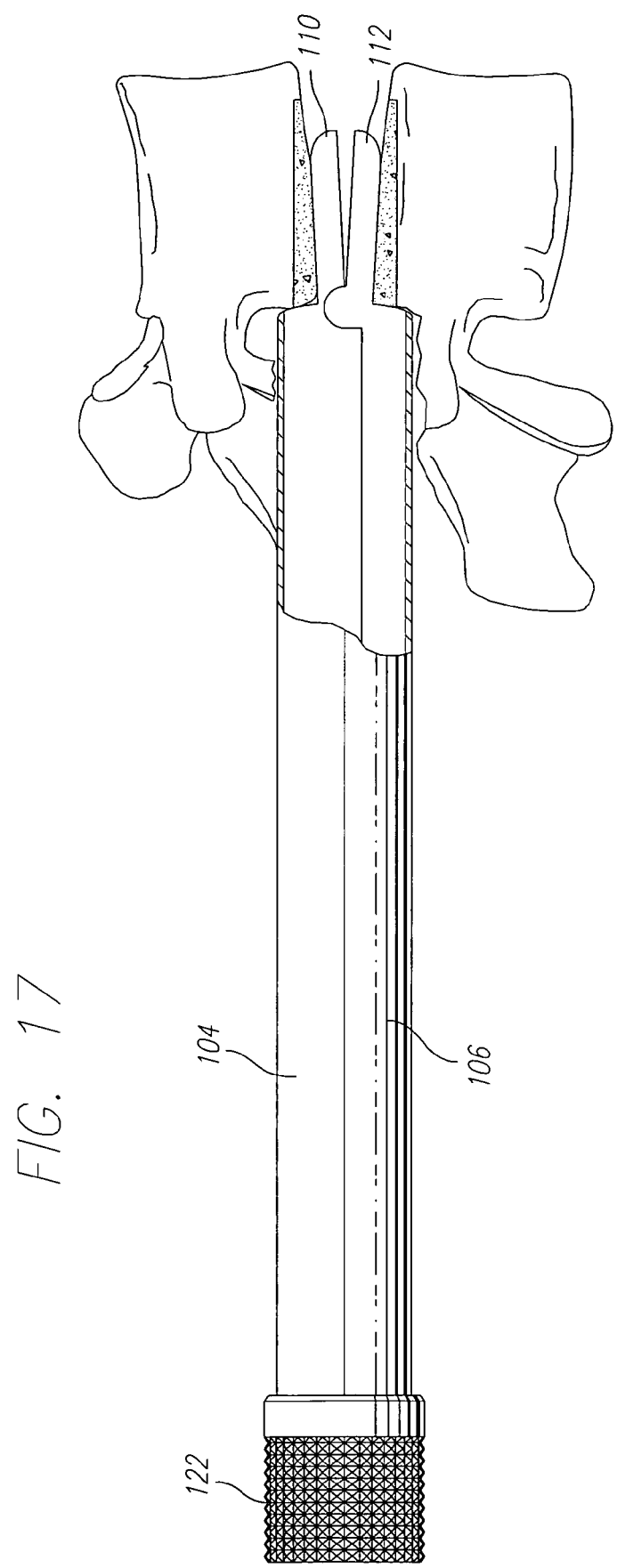
FIG. 17 is a side view of the guard inserted into the adjacent vertebral bodies with the guard in the inserted position with securing end cap on the distal end thereof and the disc penetrating extensions in the expanded position showing the portions of the vertebral end plates removed by the cutting device.

FIG. 17 shows the resected bone after removal of drill 128.

Figure 18:
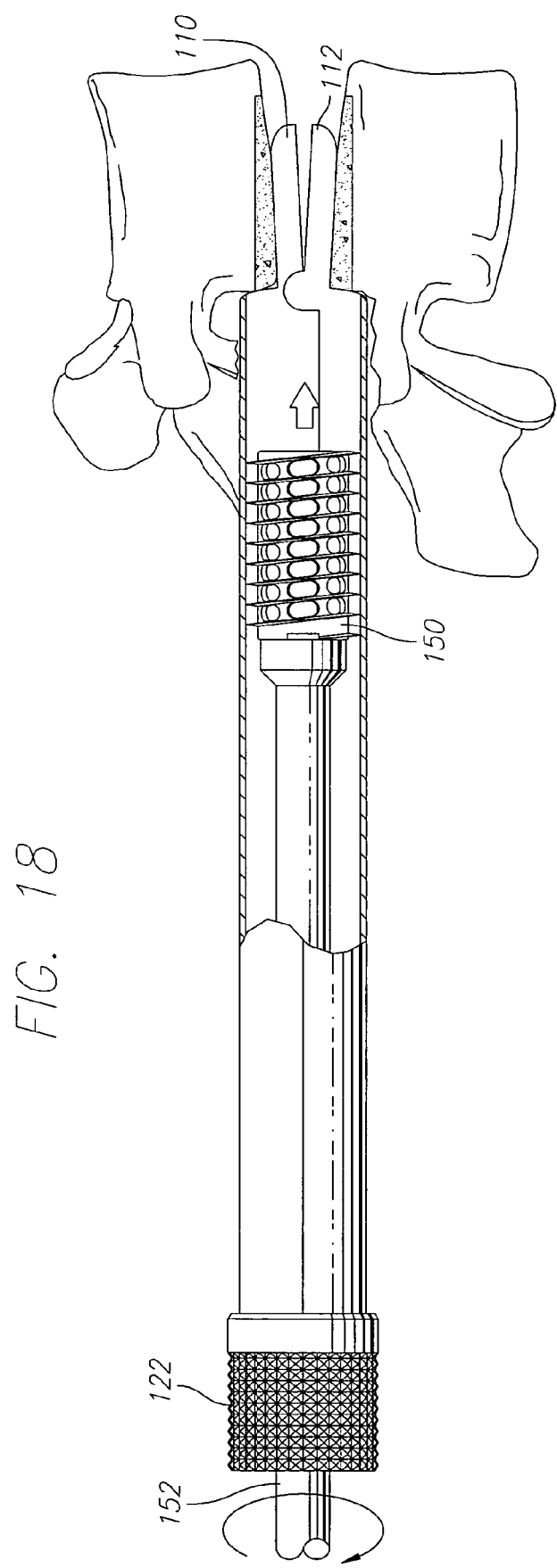
FIG. 18 is a side view of the guard of FIG. 8 with proximal end in partial cross-section showing a spinal fusion implant and inserter passing through the guard to insert an implant into the disc space between the adjacent vertebral bodies.

As best shown in FIG. 18, an implant 150, such as a threaded interbody fusion device, motion preserving device or other insert and an inserter 152 may be passed through guard 100 to insert implant 150 into the disc space between the adjacent vertebral bodies which guard may be left in place throughout the procedure.

Implant 150 may be made of artificial or naturally occurring materials suitable for implantation in the human spine. Implant 150 may also take a variety of shapes, for example, circular or oval in cross section. Implant 150 can comprise bone including, but not limited to, cortical bone. Implant 150 can also be formed of material other than bone, such as metal including, but not limited to, titanium and its alloys or ASTM material, surgical grade plastics, plastic composites, ceramics, or other materials suitable for use as an interbody implant. The plastics may be bioresorbable. Implant 150 can further be formed of bone growth promoting materials, including but not limited to, bone morphogenetic proteins, hydroxyapatite, and genes coding for the production of bone. Implant 150 can be treated with a bone growth promoting substance, can be a source of osteogenesis, or can be at least in part bioabsorbable. Implant 150 also can be formed of a porous material. Further, implant 150 may be used in combination with chemical substances and/or compounds applied at the trailing end of the implant to inhibit scar formation, and a cap may be of benefit in shielding fusion-promoting substances contained in the implant from these scar formation inhibiting chemicals and compounds.

As illustrated in FIG. 19, after implant 150 is inserted into the implantation space into contact between the adjacent vertebral bodies, body 102 of guard 100 is opened and disc penetrating extensions 110, 112 are thus placed in the first, closed position to facilitate the removal of guard 100 from the disc space. If not for the ability of the extensions to be retrieved from their lordotic inserted position, there would be no easy way to remove the guard.

In summary, a preferred method of the present invention includes: performing from a posterior approach in the lumber spine at least a partial laminectomy sufficient for access to the disc space; performing at least a partial discectomy, which more preferably provides sufficient space to receive the guard disc penetrating extensions to a depth which may be generally similar to the depth of implant 150 to be received; retracting and protecting the dural sac; inserting guard 100 with extensions 110, 112 into the disc space; inducing lordosis to the adjacent vertebral bodies; securing body 102 of guard 100 in the closed position; and inserting drill 128 through guard 100 to a desired depth. The depth of insertion may be monitored by x-ray. At this point debris may be removed by irrigation suction from within and/or about guard 100. Extensions 110, 112 are then collapsed and guard 100 is then removed. Any additional debris may be removed after removal of guard 100, again by irrigation suction. Implant 150 may be inserted through guard 100 prior to its removal from the disc space, or may be inserted after guard 100 is removed while retractors are utilized as needed to protect the proximate neural structures.

Guard 100 preferably is used for posterior lumbar interbody implantation procedures. Guard 100 includes a height, a width, and a distance between its front and rear portion. The height of body 102 is preferably between 8-25 mm and the opening height is preferably 8-20 mm. Disc penetrating extensions 110, 112 may have any shape or configuration suitable for the intended purpose disclosed herein including extensions with parallel or angled upper and lower surfaces in the closed or open position. Preferably, disc penetrating extensions 110, 112 have a combined height when closed of 6-18 mm and a length of 12-32 mm. For posterior lumbar interbody fusion, drill 128 is preferably 8-20 mm in height. These dimensions could be greater or less and still be useful for their intended purpose while still being within the inventive scope of the present invention.

Although various embodiments of the present invention have been disclosed for purposes of illustration and are for purposes of example only and not limitation, it will be understood by those of ordinary skill in the art that changes, modifications, and substitutions may be incorporated in these embodiments without departing from the spirit or scope of the present invention.

What is claimed is:

1. A method for inserting a spinal implant having at least in part upper and lower arcuate portions at least in part within and across the generally restored height of a disc space between two adjacent vertebral bodies of a human spine, the spine having a longitudinal axis, the method comprising the steps of:

positioning into the disc space between the adjacent vertebral bodies a guard having a body and an extension for insertion at least in part into the disc space and for bearing against end plates of the adjacent vertebral bodies to restore the spacing of the disc space between the adjacent vertebrae, said guard having a first portion oriented toward one of the adjacent vertebral bodies and a second portion oriented toward another of the adjacent vertebral bodies, said first and second portions being rotatably articulating relative to one another such that when said body moves from an open position to a closed position said extension moves from an insertion position to a deployed position to move the adjacent vertebral bodies apart;

rotatably articulating said guard about an axis that is generally perpendicular to the longitudinal axis of the spine to move said body from an open position to a closed position and said extension from an insertion position to a deployed position to move the adjacent vertebral bodies apart; and forming, through said guard, an opening having opposed arcuate portions across the height of the disc space and into at least a portion of the endplates of the adjacent vertebral bodies.

2. The method of claim 1, further comprising the step of performing the spinal implant surgey from a position posterior to the transverse processes of the vertebrae adjacent the disc space.

3. The method of claim 1, further comprising the steps of performing the procedure on both sides of the spinal midline of the spine and inserting two implants into the spine, each of the implants having a width less than half the width of the disc space.

4. The method of claim 1, wherein the positioning step includes placing the body of the guard in the open position to facilitate insertion and removal of the extension into and from the disc space.

5. The method of claim 1, wherein the positioning step includes the step of positioning a guard having multiple extensions for insertion into the disc space and for bearing against the end plates of the two adjacent vertebral bodies.

6. The method of claim 1, wherein the positioning step includes the step of inducing angulation to the adjacent vertebral bodies relative to one another.

7. The method of claim 1, wherein the positioning step includes the step of driving the extension into the disc space.

8. The method of claim 1, wherein the rotatably articulating step includes orienting the adjacent vertebral bodies in a predetermined relationship relative to each other.

9. The method of claim 1, wherein the rotatably articulating step includes the step of inducing lordosis to the adjacent vertebral bodies.

10. The method of claim 1, further comprising the step of securing the body of the guard in the closed position.

11. The method of claim 1, wherein the forming step includes the step of forming the implantation space with a bone removal device.

12. The method of claim 1, wherein the step of forming includes the step of inserting a bone removal device through the guard to a desired depth.

13. The method of claim 1, wherein the forming step includes the step of one of milling, drilling, reaming, and trephining the implantation space.

14. The method of claim 1, wherein the forming step includes the step of forming opposed receiving surfaces in the end plates of the vertebral bodies corresponding at least in part in size, shape, and contour to an implant to be implanted.

15. The method of claim 1, further comprising the step of inserting the implant into the implantation space.

16. The method of claim 15, wherein the inserting step includes the step of inserting the implant through the guard.

17. The method of claim 15, wherein the inserting step includes the step of inserting the implant after removing the guard from the disc space.

18. The method of claim 15, wherein the inserting step includes the step of inserting an implant having a height corresponding to the height of the implantation space formed through the guard.

19. The method of claim 15, wherein the inserting step includes the step of inserting an implant having a height greater than the maximum height of the opening between the adjacent vertebral bodies formed through the guard during the forming step.

20. The method of claim 15, wherein the step of inserting includes the step of threading the implant into the implantation space.

21. The method of claim 15, wherein the step of inserting the implant includes the step of using an implant inserter to insert the implant through the guard and into the implantation space.

22. The method of claim 21, further comprising the step of removing the implant inserter from the guard after the step of using the implant inserter to insert the implant.

23. The method of claim 15, wherein the step of inserting the implant includes the step of screwing the implant into the implantation space with an implant inserter.

24. The method of claim 15, wherein the inserting step includes inserting a spinal implant that is a spinal fusion implant for promoting fusion between adjacent vertebral bodies, the implant having at least in part arcuate upper and lower surfaces for placement between and in contact with the adjacent vertebral bodies, each of the upper and lower surfaces having at least one opening adapted to permit for the growth of bone from adjacent vertebral body to adjacent vertebral body through the implant.

25. The method of claim 15, wherein the inserting step includes inserting a spinal fusion implant having upper and lower surfaces and a hollow therebetween for holding fusion promoting substances.

26. The method of claim 15, wherein the step of inserting includes inserting an implant that is expandable into the implantation space in the spine.

27. The method of claim 15, wherein the inserting step includes the step of inserting an implant that is an inert spacer.

28. The method of claim 15, wherein the inserting step includes the step of inserting an implant that is an artificial disc.

29. The method of claim 15, wherein the inserting step includes the step of inserting an implant that is a bone graft.

30. The method of claim 15, wherein the inserting step includes inserting a spinal fusion implant with the upper and lower members being at least in part arcuate.

31. The method of claim 15, wherein the inserting step includes inserting an implant having surface projections configured to resist expulsion of the implant from the implantation space.

32. The method of claim 15, further comprising the step of loading the implant with fusion promoting substance.

33. The method of claim 32, wherein the step of loading includes the step of compressively loading the implant with fusion promoting substance.

34. The method of claim 32, wherein the loading step includes loading the implant with the fusion promoting substance being selected from one of bone, bone derived products, demineralized bone matrix, ossifying proteins, bone morphogenetic protein, hydroxyapatite, and genes coding for the production of bone.

35. The method of claim 32, further comprising the step of retaining the fusion promoting substance within the implant after the step of loading.

36. The method of claim 35, wherein the step of retaining includes the step of attaching a cap to the implant to retain the fusion promoting substance.

37. The method of claim 15, further comprising the step of treating the implant with a fusion promoting substance.

38. The method of claim 15, wherein the implant is in combination with a chemical substance adapted to inhibit scar formation.

39. The method of claim 15, wherein the implant is in combination with an antimicrobial material.

40. The method of claim 15, wherein the inserting step includes inserting an implant comprising a fusion promoting substance.

41. The method of claim 15, wherein the inserting step includes inserting an implant comprising a bone ingrowth surface.

42. The method of claim 15, wherein the inserting step includes the step of inserting an implant comprised at least in part of one of bone and bone growth promoting material.

43. The method of claim 15, wherein the implant is in conibination with at least one of a fusion promoting substance, bone, bone growth promoting material, bane derived products, demineralized bone matrix, ossifying proteins, bone morphogenetic protein, hydroxyapatite, and genes coding for the production of bone.

44. The method of claim 1, further comprising the steps of collapsing the extensions and removing the guard from the disc space.

* * * * *

UNITED STATES PATENT AND TRADEMARK OFFICE
CERTIFICATE OF CORRECTION

PATENT NO. : 7,314,468 B2
APPLICATION NO. : 10/809149
DATED : January 1, 2008
INVENTOR(S) : Gary K. Michelson It is certified that error appears in the above-identified patent and that said Letters Patent is hereby corrected as shown below:

<u>Column 12</u>:
Line 6: change "surgey" to --surgery--.

<u>Column 14</u>:
Line 33: change "conibination" to --combination--; and
Line 34: change "bane" to --bone--.

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,314,468 B2 |
| APPLICATION NO. | : 10/809149 |
| DATED | : January 1, 2008 |
| INVENTOR(S) | : Gary K. Michelson |

Page 1 of 1

It is certified that error appears in the above-identified patent and that said Letters Patent is hereby corrected as shown below:

<u>Column 12</u>:
Line 6: change "surgey" to --surgery--.

<u>Column 14</u>:
Line 33: change "conibination" to --combination--; and
Line 34: change "bane" to --bone--.

Signed and Sealed this

Thirteenth Day of May, 2008

JON W. DUDAS
*Director of the United States Patent and Trademark Office*